United States Patent [19]

Guillemin et al.

[11] 4,280,953
[45] Jul. 28, 1981

[54] GLYCOSYLATED ANALOGS OF SOMATOSTATIN

[75] Inventors: Roger C. L. Guillemin, La Jolla; Solange Lavielle, San Diego; Paul E. Brazeau, Jr., San Diego; Nicholas C. Ling, San Diego; Robert A. Benoit, San Diego, all of Calif.

[73] Assignee: The Salk Institute for Biological Studies, San Diego, Calif.

[21] Appl. No.: 92,647

[22] Filed: Nov. 8, 1979

[51] Int. Cl.³ .................... C07C 103/52; A61K 37/00
[52] U.S. Cl. .............................. 260/112.5 S; 424/177
[58] Field of Search .................. 260/112.5 S; 424/177

[56] References Cited

U.S. PATENT DOCUMENTS 3,845,204  10/1974  Grant ............................. 260/112.5 S

*Primary Examiner*—Delbert R. Phillips
*Attorney, Agent, or Firm*—Fitch, Even, Tabin, Flannery & Welsh

[57] ABSTRACT

Somatostatin (SS) is modified to incorporate a carbohydrate moiety in the peptide chain by linkage to either Asn, Ser or Thr. The modified SS peptide analog may have the formula:

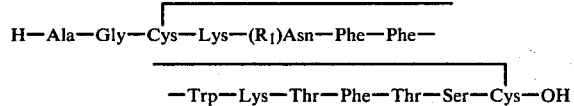

wherein $R_1$ is preferably a hexose or amino-hexose, such as glucose or N-acetylglucosamine. Alternatively, the carbohydrate can be linked to Ser or Thr by an ether bond. Such glycosomatostatins have an extended biological half-life compared to the parent peptide and substantially the same potency. Modifications and substitutions with respect to other amino acid residues in the chain can be made in the glycopeptides, for the purpose of increasing the effectiveness of SS analogs in other ways, and such increased effectiveness is a characteristic of the glycosomatostatin along with its longer-acting biological effect.

5 Claims, No Drawings

GLYCOSYLATED ANALOGS OF SOMATOSTATIN

The invention described herein was made in the course of work under a grant or award from the Department of Health, Education and Welfare.

The present invention relates generally to modified somatostatin peptides having a long-acting inhibitory influence on (1) secretion of growth hormone by the pituitary gland, (2) secretion of glucagon and insulin by the pancreas, (3) secretion of vasoactive intestinal polypeptides, secretin, gastrin, and gastric acid in human and animals. More particularly, the present invention is directed to peptides which are as effective as somatostatin and known somatostatin analogs in the inhibition of hormone secretions, but which are substantially longer-acting.

BACKGROUND OF THE INVENTION

Somatostatin (SS) and various acylated derivatives of SS are described in U.S. Pat. No. 3,904,595 to Guillemin et al. SS is a tetradecapeptide having the following structure, with amino acid moieties numbered from left to right in accordance with usual nomenclature:

$$\text{H—Ala—Gly—Cys—Lys—Asn—Phe—Phe—Trp—Lys—Thr—Phe—Thr—Ser—Cys—OH}$$
$$\text{1 \quad 2 \quad 3 \quad 4 \quad 5 \quad 6 \quad 7 \quad 8 \quad 9 \quad 10 \quad 11 \quad 12 \quad 13 \quad 14}$$

U.S. application, Ser. No. 675,149, filed Apr. 9, 1976, describes further SS analogs wherein substitutions for amino acid moieties in the backbone of SS provide a peptide which is therapeutically valuable when introduced, either directly or indirectly, into the bloodstream of mammals to inhibit the secretion of growth hormone from the pituitary gland and insulin and gluagon. from the pancreas. These peptides have D-Trp substituted for Trp in the eight position of SS and may have Ala substituted in the five position or simply have this position deleted.

U.S. Pat. No. 4,133,782, issued Jan. 9, 1979 to Vale et al., describes other analogs of SS which possess dissociated biological activity in respect to the inhibition of growth hormone, insulin or glucagon secretion. Examples of these peptides include des-Asn$^5$-[D-Trp$^8$]-SS; [D-Ser$^{13}$]-SS; [D-Trp$^8$,D-Ser$^{13}$]SS; [D-Cys$^{14}$]-SS;.

U.S. Pat. No. 4,105,603, describes peptides having fewer amino acid residues than SS but which still possess biological activity in respect to the inhibition of growth hormone, insulin or glucagon secretion. A number of nonapeptides and octapeptides are illustrated, some of which have dissociated activity. The octapeptide covered by this patent having the formula:

$$\text{H—Cys—Phe—Phe—D—Trp—Lys—Thr—Phe—Cys—OH}$$

shows prolonged inhibitory activity on the secretion of insulin, glucogon pancreatic polypeptide and gastrin in human subjects following subcutaneous administration.

BRIEF SUMMARY OF THE INVENTION

From the foregoing discussion of the SS art, it is apparent that a vast number of SS analogs have been developed which have various potencies, relative to SS, in respect to inhibition of the release of growth hormone, glucagon, insulin, gastrin and gastric acid in warm blooded animals. The novel peptides of the present invention are based on the discovery that, by incorporating a carbohydrate moiety into the peptide SS, somatostatin peptides are provided having a longer acting inhibitory activity. The carbohydrate moiety is linked to either Asn, Ser or Thr which appears in the SS peptide chain. Convenient carbohydrate moieties for incorporation into an SS peptide are the pentose and hexose monosasccharides, particularly those having the pyranose structure, such as glucose and fructose. Amino-sugars, i.e., pentoses and hexoses, having an amide group attached to the 2-position carbon atom can also be employed. Accordingly, the invention provides SS analogs wherein at least one amino acid residue selected from the group consisting of Asn, Ser and Thr is linked with a carbohydrate moiety, particularly one having a pyranose structure.

DETAILED DESCRIPTION OF THE PREFERRED EMBODIMENTS

The SS analogs of the present invention may be characterized by the general formula:

$$\text{H—Ala—Gly—Cys—Lys—Asn(R}_1\text{)—Phe—Phe—Trp—Lys—Thr(R}_2\text{)—Phe—Thr(R}_3\text{)—Ser(R}_4\text{)—Cys—OH}$$

wherein $R_1$, $R_2$, $R_3$ and $R_4$ are either hydrogen or a carbohydrate moiety selected from the group consisting of pentoses, amino-pentoses, hexoses and amino-hexoses, monasaccharides, provided that $R_1$, $R_2$, $R_3$ and $R_4$ are not simultaneously hydrogen. The SS analogs are preferably prepared by solid-phase synthesis using a protected amino acid which is already linked to the carbohydrate moiety. Thus, one or more glyco-amino acids can easily be incorporated into a particular SS analog, as desired.

Glycosolating Asn in the 5-position has proved effective in extending the biological half-life of SS and analogs of SS and is readily synthesized by linkage via the ω-amide group of Asn. SS analogs wherein other carbohydrate moieties are linked to Asn are also effective in extending the duration of potency. An appropriate carbohydrate moiety having an amino group on the C-1 position is condensed with aspartic acid having its α-amino group protected with a TFA-labile protecting group, e.g., BOC, and its α-carboxyl group in the form of a suitable ester, e.g., benzyl ester. accordingly, SS analogs including a monosacchharide linked to Asn are preferred.

Linkages to either Ser or Thr via the β-hydroxy group can also be effected, and such linked moieties can also be employed in solid-phase peptide synthesis. For example, serine having its α-amino group protected with BOC and having its carboxyl group in the form of a suitable ester is linked to the chlorinated 1-position carbon atom of N-acetyl-α-D-Glucosamine by an ether linkage, using a chemical reaction known in the art. A similar linkage is effected to Thr via its free hydroxyl group.

Hexoses and amino-hexoses, such as N-acetylglucosamine, have been investigated and are effective in decreasing the metabolic rate of clearance of the SS analog and thus extending its biological half-life. Those having the pyranose structure, e.g., glucose, are presently considered to be best suited. N-acetyl-α-D-glucosamine is preferred.

It has been found that the inclusion of a carbohydrate moiety, such as N-acetyl-α-D-glucosamine, in an analog of SS does not significantly change its biological potency with respect to the inhibition of secretion of hormones. Accordingly it is considered that the invention is applicable to any analogs of SS which contain Asn, Ser and/or Thr. Similarly, linkage to the particular amino-acid can be effected. The abbreviations used are those universally accepted for the amino acids. For purpose of the examples, if no prefix is given, the amino acid should be understood to be in the L-form; however, as indicated above, substitution by the D-isomer form of one or more of the amino acid residues does not remove the peptide from applicability of the invention.

The peptides may also be prepared and administered in the form of pharmaceutically acceptable nontoxic salts, such as acid addition salts or metal complexes, e.g., with zinc, iron or the like. Illustrative of such acid addition salts are hydrochloride, hydrobromide, sulphate, phosphate, maleate, acetate, citrate, benzoate, succinate, malate, ascorbate, tartrate and the like.

Also considered to be within the scope of the present invention are intermediates of the formula:

$(X^1)$—Ala—Gly—Cys$(X^2)$—Lys$(X^3)$—$(R_1)$Asn—Phe—Phe—Trp—Lys$(X^4)$-$(R_2)$Thr$(X^5)$—Phe—$(R_3)$Thr$(X^6)$—$(R_4)$Ser$(X^7)$—Cys$(X^8)$—$X^9$ wherein: $X_1$ is either hydrogen or an α-amino protecting group. The α-amino protecting groups contemplated by $X_1$ are those known to be useful in the art in the step-wise synthesis of polypeptides. Among the classes of α-amino protecting groups covered by $X^1$ are (1) acyl-type protecting groups, such as formyl, trifluoroacetyl, phthalyl, toluenesulfonyl(tosyl), benzensulfonyl, nitrophenylsulfenyl, tritylsulfenyl, o-nitrophenoxyacetyl, chloroacetyl, acetyl, and α-chlorobutyryl; (2) aromatic urethan-type protecting groups, such as benzyloxycarbonyl (CBZ) and substituted CBZ, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl (trityl), benzyl; (7) trialkylsilane groups, such as trimethylsilane. The preferred α-amino protecting group is BOC.

$X^2$ and $X^8$ are each a protecting group for Cys or D-Cys selected from the group consisting of p-methoxybenzyl, p-methylbenzyl, acetamidomethyl, trityl and and benzyl (Bzl). The preferred protecting group is p-methoxybenzyl. $X^2$ and/or $X^8$ can be hydrogen which means that there is no protecting group on the sulfur group.

$X^3$ and $X^4$ are each a protecting group for the side chain amino substituent of Lys. Illustrative of suitable side chain amino protecting groups are benzyl (Bzl), chlorobenzyloxycarbonyl (Cl—CBZ), benzyloxycarbonyl (Z), tosyl (TOS), t-amyloxycarbonyl and BOC. The selection of a side chain amino protecting group is not critical except that it must be one which is not removed during deprotection of the α-amino groups during the synthesis. Hence, the α-amino protecting group and the side chain amino protecting group cannot be the same.

$X^5$, $X^6$ and $X^7$ are protecting groups for the hydroxyl group of Thr and Ser and are selected from the group consisting of acetyl, benzoyl, tert-butyl, trityl, tetrahydropyranyl, Bzl, 2,6-dichlorobenzyl and CBZ. The preferred protecting group is Bzl. $X^5$ and/or $X^6$ and/or $X^7$ can be hydrogen, which means there is no protecting group on the hydroxyl group, provided however that when any of $R_2$, $R_3$ and $R_4$ are present, the respective protecting group is not present. $R_1$, $R_2$, $R_3$ and $R_4$ are as previously defined.

$X^9$ is selected from the class consisting of OH, OCH$_3$, esters, amides, hydrazides and benzyl ester or hydroxymethyl ester anchoring bond used in solid phase synthesis linked to a solid resin support represented by the formulae:

—O—CH$_2$—polystyrene resin support and

O—CH$_2$—benzyl-polystyrene resin support

The polymer is preferably a copolymer of styrene with about 0.5 to 2% divinyl benzene as a cross linking agent which causes the polystyrene polymer to be completely insoluble in certain organic solvents. In the formula, at least one of $X^1$, $X^2$, $X^3$, $X^4$, $X^5$, $X^6$, $X^7$, and $X^8$ is a protecting group.

In selecting a particular side chain protecting group to be used in the synthesis of the peptides, the following rules are followed: (a) the protecting group must be stable to the reagent and under the reaction conditions selected for removing the α-amino protecting group at each step of the synthesis, (b) the protecting group must retain its protecting properties and not be split off under coupling conditions, and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, J. Am. Chem. Soc., 85, p 2149 (1964), although other equivalent chemical syntheses known in the art can also be used. Solid-phase syntheses is commenced from the C-terminal end of the peptide by coupling a protected α-amino acid to a suitable resin. Such a starting material can be prepared by attaching α-amino- and S-protected Cys to a chloromethylated resin or a hydroxymethyl resin. The preparation of the hydroxymethyl resin is described by Bodansky et al., Chem. Ind. (London) 38, 1597–98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1–6.

Cys protected by BOC and by p-methoxybenzyl is coupled to the chloromethylated resin according to the procedure of Monahan and Gilon, Biopolymers 12, pp 2513–19, 1973. Following the coupling of BOC-(p- methoxybenzyl) (Cys) to the resin support, the α-amino protecting group is removed, as by using trifluoroacetic acid (TFA) in methylene chloride, TFA alone or HCl in dioxane. The deprotection is carried out at a temperature between about 0° C. and room temperature. Other standard cleaving reagents and conditions for removal of specific α-amino protecting groups may be used as described in Schroder & Lubke, "The Peptides," 1 pp 72–75 (Academic Press 1965).

After removal of the α-amino protecting group of Cys, the remaining α-amino- and side chain-protected amino acids are coupled step-wise in the desired order to obtain the intermediate compound defined hereinbefore, or as an alternative to adding each amino acid separately to the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are: (1) carbodiimides, such as N,N'-diisopropyl carbodiimide, N-ethyl-N'-(3-dimethylaminopropyl)carbodiimide; (2) cyanamides such as N,N'-dibenzylcyanamide; (3) keteimines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) nitrogen-containing heterocyclic compounds having a hydroxy group on one ring nitrogen, such as N-hydroxyphthalimide, N-hydroxysuccinimide and 1-hydroxybenzotriazole (HOBT). Other activating reagents and their use in peptide coupling are described by Schroder & Lubke supra, in Chapter III and by Kapoor, J. Phar. Sci., 59, pp 1–27 (1970).

Each protected amino acid or amino acid sequence is introduced into the solid phase reactor in about a fourfold excess, and the coupling is carried out in a medium of dimethylformamide (DMF):$CH_2Cl_2$ (1:1) or in DMF or $CH_2Cl_2$ alone. In cases where incomplete coupling occurred, the coupling procedure is repeated before removal of the α-amino protecting group prior to the coupling of the next amino acid. The success of the coupling reaction at each stage of the synthesis is monitored by the ninhydrin reaction, as described by E. Kaiser et al., Anal. Biochem. 34, 595 (1970).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$ and $X^8$ and the α-amino protecting group $X^1$, to obtain the peptide in its linear form. The cyclic form of the peptide is obtained by oxidizing using a ferricyanide solution or the like in accordance with known procedures or preferably as described in U.S. patent application Ser. No. 926,491, filed July 19, 1978 in the name of Jean E. F. Rivier et al.

As an alternative route, the intermediate peptide may be separated from the resin support by alcoholysis after which the recovered C-terminal methyl ester is converted to the acid by hydrolysis. Any side chain protecting groups may then be cleaved as previously described or by other known procedures, such as catalytic reduction (e.g. Pd on $BaSO_4$) using conditions which will keep the Trp moiety intact. When using hydrogen fluoride for cleaving, anisole is included in the reaction vessel as a scavenger.

As earlier indicated, the combination of a carbohydrate moiety, particularly one having the pyranose structure, and the desired amino acid (one having its α-amino group protected) is first synthesized, and this combination is then coupled to the existing chain carried by the resin support at the appropriate step in the stepwise synthesis.

EXAMPLE I

A glycoasparagine derivative having an acid-labile N-protecting group suitable for introduction into a peptide being synthesized by solid phase techniques is synthesized as set forth hereinafter for introduction thereinto at the appropriate step. The derivative in question is 1-amino-2,3,4,6-tetra-O-acetyl-β-D-glucopyranosyl—N—BOC—L-Asnβ-carboxamide.

Acetic anhydride (50 g) and 65 g of dry pyridine are cooled to 0° C., and 10 g of powdered, anhydrous α-D-glucose is added. The suspension is stirred at 0° until dissolution and allowed to stand 18 hours at room temperature. Cooling with ice and water causes α-D-glucopyranose pentaacetate to crystallize after a few minutes. Purification is effected by recrystallization from 95% ethanol.

The crystals are dissolved in chloroform (100 ml) and added to 30% hydrogen bromide in acetic acid (180 ml). After 2 hours at room temperature, it is poured into ice-water, and the mixture is extracted with dichloromethane. The extract is successively washed with cold water and cold saturated bicarbonate, and thereafter it is dried and evaporated. Purification is effected by recrystallization from $CH_2Cl_2$-$Et_2O$ to yield Tetra-O-acetyl-α-D-glucopyranosyl bromide.

11 g of 2,3,4,6-tetra-O-acetyl-α-D-glucopyranosyl bromide is dissolved in acetone (180 ml) and added dropwise, in 30 min, to a cold solution of sodium azide (6.5 g) in water (100 ml). After stirring at 0°, for 150 min, the solution is kept at room temperature for 180 min. The mixture is extracted with $CH_2Cl_2$. Recrystallization from $CH_2Cl_2$-$Et_2O$ yields 2,3,4,6-tetra-O-acetyl-2-α-D-glucopyranosyl azide.

Platinum oxide (200 mg) is added to a solution of 2.5 g of the azide in 200 ml of absolute ethanol, and the suspension was shaken with hydrogen gas for 1 hour at atmospheric pressure and room temperature. After the suspension is filtered three times on a Celite column, the filtrate is evaporated to dryness. Recrystallization from $CH_2Cl_2$-$Et_2O$ yields 2,3,4,6-tetra-O-acetyl-β-D-glucopyranosyl amine.

The amine is then condensed with N-BOC-L-aspartic-α-benzylester to yield the desired, protected glycoasparagine under the following conditions. α-benzyl N-BOC-L-aspartate (0.834 g) and HOBT (0.593 g.) are dissolved in 5 ml of 50% DMF/$CH_2Cl_2$. DCCI is added at 0° C., and after 5 min. the solution is filtered into a solution of 1-amino-2,3,4,6-tetra-O-acetyl-β-D-glucopyranose (0.806 g) in $CH_2Cl_2$ (5 ml). After stirring at room temperature for 2 hours and washing with weak acid and base, the solvent is evaporated, and the remaining syrup is chromatographed on a column of silica gel (100 g) with CHCl$_3$:EtOAc (6:4) to yield 1.23 g (83%) of the acetylated glucoasparagine ester. Recrystallization from CH$_2$Cl$_2$-Et$_2$0 gives a compound and having an m.p. 170°–172° C. and optical rotation of $[\alpha]_D^{23}$ +22° (1,CHCl$_3$) and having the formula 2,3,4,6-tetra-O-acetyl-1-β(α-benzyl-N-BOC-L-aspartamido)-1-deoxy-D-glucose pyranose.

The glucoasparagine ester (0.978 g) is hydrogenated in ethanol-water (220 ml, 10:1) over 10% palladium on charcoal (0.15 g) at room temperature and atmospheric atmospheric pressure for 5 hours. After filtration over a celite column and evaporation of the solvent, a white amorphous powder is obtained (0.735 g.) which has an optical rotation of $[\alpha]_D^{23}$+31° (1,CHCl$_3$) and which is 1-amino-2,3,4,6-tetra-O-acetyl-β-D-glucopyranosyl-N-BOC-L-Asn-β-carboxamide—(I).

EXAMPLE II

An analog of SS containing the compound (I) in the 5-position is synthesised in a stepwise manner on a chloromethylated resin in the form of fine beads (20–70microns in diameter). The resin was prepared by copolymerization of styrene with one to two percent divinylbenzene, and the benzene rings in the resin were chloromethlated in a Friedel-Crafts reaction with chloromethyl methyl ether and stannic chloride to contain 0.5 to 2 millimoles of chlorine per gram of resin in a reactive benzyl chloride type of linkage.

Somatostatin for use as a control and having the structure:

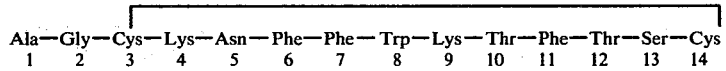

Ala—Gly—Cys—Lys—Asn—Phe—Phe—Trp—Lys—Thr—Phe—Thr—Ser—Cys
 1    2    3    4    5    6    7    8    9   10   11   12   13  14 is synthesized along with the SS analog of the invention including the glucoasparagine (I) synthesized in Example I.

The potassium salt of the BOC-(p-methoxybenzyl) derivative of Cys is linked to the resin by heating at 80° C. for 2 hours in DMSO in the presence of potassium tertiobutoxide.

After deprotection and neutralization, the peptide chain is built on the resin. Deprotection, neutralization and addition of each amino acid is performed as indicated hereinafter. The Boc derivative of each amino acid is used. After deprotection of the Cys residue according to Schedule set forth in U.S. Pat. No. 4,105,603, the Boc derivative of Ser is next added along with DCCI as a coupling agent. The side chains of Ser and Thr are protected with Bzl. 2-Cl-Z is used as the protecting group for the Lys side chain. When SS is synthesized as a control, Asn is coupled as its p-nitrophenyl ester in DMF overnight, and the glycosylated Asn (I) is coupled using 1.0 eqt, DCCI and 1.5 eqt. HOBT in 50% DMF/CH$_2$Cl$_2$ for overnight.

Cleavage of the peptide from the resin and deprotection of the side chain protecting groups of the peptide is performed in HF in the presence of anisole. After elimination of hydrofluoric acid under high vacuum, the resin-peptide is washed with ether.

The dried resin is immediately extracted with 25% acetic acid, and the remaining peptide solution is diluted with degassed H$_2$O. The pH of the solution is adjusted to about 6.8 with NH$_4$OH, and the solution is added dropwise under stirring to a potassium ferricyanide solution to form the disulfide bond. After oxidation, the peptides are chromatographed on both anion- and cation-exchange resins and lyophilized. The peptides are then submitted to gel filtration on Sephadex G-25 fine, followed by de-O-acetylation of the sugar moiety with a saturated solution of ammonia in methanol. Final purification of the peptide (II) is carried out by partition chromatography on Sephadex G-25 fine, with the eluent system 1-butanol-acetic acid-water (4:1:5). The optical rotation is measured as $[\alpha]_D^{23}$= =29.3 (c=1 in 1% acetic acid). Amino acid analysis showed the expected ratio for the different amino acids. Trypsin digestion yields the pentapeptide fragment comprising residues 5 to 9, which on TLC and HPLC showed the same R value and retention time as the corresponding model peptide [Glc-Asn]-Phe-Phe-Trp-Lys-OH, which had been synthesized separately and whose structure had been determined by mass spetrometry.

EXAMPLE III

The general procedure procedure of Example I is repeated to synthesize a glycoasparagine derivative having the formula 1-amino-2-acetamido-3,4,6-tri-O-acetyl-2-deoxy-β-D-glucopyranosyl-N-BOC-L-Asn-β-carboxamide.

Acetic anhydride (50 g) and 65 g of dry pyridine are cooled to 0° C., and 10 g of powdered, anhydrous-D-glucosamine is added. The suspension is stirred at 0° until dissolution and allowed to stand 18 hours at room temperature. Cooling with ice and water is followed by extraction with CH$_2$Cl$_2$ and washing with cold bicarbonate solution. After drying, the solvent is evaporated. Recrystallization from CH$_2$Cl$_2$-Et$_2$0 yields 2-acetamido-1,3,4,6-tetra-O-acetyl-α-D-glucose.

The crystals are added to 50 g of glacial acetic acid saturated with dry hydrogen bromide at 0° C. After standing overnight at room temperature, 80 ml. of CHCl$_3$ are added. The mixture is shaken and poured into ice-water. The aqueous layer is extracted with chloroform and added to the main chloroform layer. The organic solution is successively washed with cold saturated bicarbonate and cold water, and thereafter it is dried and evaporated to a pale yellow syrup. Addition of a small volume of EtOAc and Et$_2$O yields 2-acetamido-3,4,6-tri-O-acetyl-α-D-glycopyranosyl bromide which is immediately converted into the azide.

7.8 g of this bromide is dissolved in chloroform (240 ml) and added to a cold solution of sodium azide (9.5 g) in dry DMF (240 ml). After stirring at room temperature for 5 hours, the pale yellow syrup crystallizes on addition of Et$_2$O. Recrystallization from CH$_2$Cl$_2$-Et$_2$O yields 2-acetamido-3,4,6-tri-O-acetyl-2-deoxy-β-D-glucopyranosyl azide.

Platinum oxide d (2.6 g) is added to a solution of 2.6 g of the azide in 150 ml of absolute ethanol, and the suspension is shaken with hydrogen gas for 1.5 hours at atmospheric pressure and room temperature. After the suspension is filtered three times on a celite column, the filtrate is evaporated to dryness. Recrystallization from CH$_2$Cl$_2$-Et$_2$O yields 2-acetamido-3,4,6-tri-O-acetyl-2-deoxy-β-D-glucopyranosyl amine.

The amine is then condensed with N-BOC-L-aspartic-α-benzyl ester to yield the desired, protected glycoasparagine under the following conditions. α-benzyl N-BOC-L-aspartate (0.9 g) and HOBT (0.6 g.) are dissolved in 5 ml of 50% DMF/CH$_2$Cl$_2$. DCCI is added at 0° C., and after 5 min. the solution is filtered into a solution of 1-amino-2-acetamido-3,4,6-tri-O-acetyl-β-D-glucopyranose (0.9 g) in CH$_2$Cl$_2$ (5 ml). After stirring at room temperature for 2 hours and washing with weak acid and base, the solvent is evaporated, and the remaining syrup is chromatographed on a column of silica gel (100 g) with EtOAc to yield 1.226 g of the acetylated glycoasparagine ester. Recrystallization from CH$_2$Cl$_2$-Et$_2$O gives a compound having a M.P. 157°–158° C. and an optical rotation of $[\alpha]_D^{23}+6.5°$ (1,CHCl$_3$) having the formula 2-acetamido-3,4,6-tri-O-acetyl-1-β(α-benzyl-N-BOC-L-β-aspartamido)-1,2-dideoxy-D-glycopyranose.

The glucoasparagine ester (1.2 g) is hydrogenated in ethanol-water (220 ml, 10:1) over 10% palladium on charcoal (0.15 g) at room temperature and atmospheric pressure for 5 hours. After filtration over a celite column and evaporation of the solvent, a white amorphous powder is obtained (0.92 g) which has an m.p. 193°–195° C. and optical rotation of $[\alpha]_D^{23}+23.40°$ (1,CHCl$_3$) and which is 1-amino-2-acetamido-3,4,6-tri-O-acetyl-2-deoxy-β-D-glucopyranosyl-N-BOC-L-Asn-β-carboxamide (III)

EXAMPLE IV

The procedure of Example II is repeated, substituting the compound (III) for the compound (I) to produce an SS analog (IV) having the compound (III) in the 5-position.

Testing of the compounds (II) and (IV) and SS is carried out with respect to the inhibition of secretion of growth hormone (GH) both in vitro and in vivo. When tested in vitro using a culture made from the anterior pituitaries of male rats, the activity of the two glycopeptides (II) and (IV) is about 0.1% and 1% compared to SS. When tested in vivo using male rats in which secretion of growth hormone (GH) is acutely stimulated by the injection of morphine sulfate, there is no substantial difference between the three compounds with respect to potency to inhibit the spontaneous secretion of GH; however, the duration of effectiveness of glycopeptides (II) and (IV) is greater than SS.

EXAMPLE V

A glycoserine derivative having an acid-labile-α-protecting group, suitable for use in the solid phase synthesis of a peptide, is formed in the following manner. The derivative has the formula

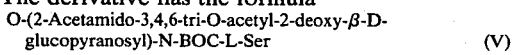

O-(2-Acetamido-3,4,6-tri-O-acetyl-2-deoxy-β-D-glucopyranosyl)-N-BOC-L-Ser (V)

Acetyl chloride (70 ml) and 25 g of dry 2-acetamido-2-deoxy-α-D-glucose is stirred for 16 hours without external heating at room temperature. The mixture boils spontaneously during the first hour of reaction and ultimately produces a viscous, clear, slightly pinkish liquid. CH$_2$Cl$_2$ is added, and the solution is poured with vigorous stirring onto 200 g of cracked ice and 50 ml of H$_2$O. The mixture is transferred to a separatory funnel and shaken. The organic solution is drawn off without delay into a beaker containing ice and saturated bicarbonate. After neutralization is completed, the organic layer is separated and added to a flask containing 20 g anhyd. MgSO$_4$. The filtrate is concentrated to 50 ml in a rotary evaporator at 50°, and dry ether (300 ml) plus petroleum ether (50 ml) are rapidly added with swirling to cause crystallization to begin. The flask is stoppered and set aside for 12 hours at room temperature. The solid is collected to yield 23.5 g of 2-Acetamido-3,4,6-tri-O-acetyl-2-deoxy-α-D-glucopyranosyl chloride.

To a solution of N-BOC-L-serine (812 g, 40 mmoles) in 42 ml DMSO are added 42 ml of a 1 M potassium hydroxide ethanolic solution. After 5 min. at room temperature, 9.52 ml of benzyl bromide 9.52 are added. The mixture is stirred for 15 hours, at room temperature. After addition of CH$_2$Cl$_2$ (300 ml), the solution is washed with H$_2$O, dried over MgSO$_4$ and the solvents are evaporated. The yellowish syrup (10.75 g) is further purified by chromatography on a silica gel column (300 g; CHCl$_3$: AcOEt (8:2)) to yield 8.02 g (68%) of the benzyl ester which crystallizes upon addition of petroleum ether. m.p. 69°–70°. Recrystallization from Et$_2$O-petroleum ether yields N-BOC-L-serine benzyl ester having m.p. 69–70 and optical rotation $[\alpha]_D^{23}-18.9°$ (c=2, MeOH).

To a solution of 2.95 g. of the ester in benzene (100 ml), mercuric cyanide (3.04 g) and benzene (25 ml) are added, and 25 ml of benzene are distilled off. The glucopyranosyl chloride is added (4.40 g), and the stirred mixture is boiled under reflux for 18 hrs. and then kept at room temperature for 24 hrs. The dark-orange solution is evaporated, and the residue extracted with CH$_2$Cl$_2$. The organic layer is then washed with 10% KI solution, H$_2$O and dried over MgSO$_4$. The residual oil (6.07 g) is purified by chromatography on a silica gel column (300 g) to afford 1.7 g of a slightly yellow oil which crystallizes after addition of ether (27%). Recrystallization from CH$_2$CL-Et$_2$O yields 0-(2-Acetamido-3,4-6-tri-O-acetyl-2-deoxy-β-D-glucopyranosyl)-N-(t-butyloxycarbonyl)-L-serine benzyl ester having m.p. 137°–138° and optical rotation $[\alpha]_D^{23}-12.1°$ (CHCl$_3$).

A solution of the glycosylated Ser benzyl ester (1.31 g) in 9:1 ethanol-water (250 ml) is hydrogenated in the presence of 10% palladium on charcoal (0.250 g) at atmospheric pressure and at room temperature for 5 hours. After filtration on a celite column, the filtrate is evaporated at 40° C. to yield a white amorphous powder (1.01 g) O-(2-Acetamido-3,4,6-tri-O-acetyl-2-deoxy-β-D-glucopyranosyl)-N-(t-butyloxycarbonyl)-L-serine (V) having m.p. 157°–159° and optical rotation $[\alpha]_D^{23}+3°$ (CHCl$_3$).

EXAMPLE VI

The procedure of Example II is generally repeated substituting the compound (V) for Ser for attachment to the Cys residue initially attached to the resin, and using the p-nitrophenylester of Asn instead of compound (I) to produce an SS-analog (VI) having the compound (V) in the 13-position. The analog [NacGlc-Ser$^{13}$]-SS has optical rotation $[\alpha]_D^{23}:-36.2°$ (C=1, 1% AcOH). Testing of the glycopeptide (VI) shows results about the same as for compound (II) in the inhibition of the secretion of GH.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. For example, glycoasparagine and glycoserine can be incorporated in the same SS analog, and either or both of such moieties can be incorporated along with one or two residues of glycothreonine. Likewise, various β-isomers of pentoses, amino-pentoses, hexoses or amino-hexoses can be linked to Asn and α- or β-isomers of the same or different pentoses, hexoses or amino-monosaccharides can be linked to Ser and/or Thr. Moreover, substitutions and modifications of SS can be made in the basic analogs so long as at least one residue of Asn, Ser and Thr remains in the basic peptide formula to which the carbohydrate linkage can be effected.

Various features of the invention are emphasized in the claims which follow.

What is claimed is:

1. A somatostatin peptide having the formula

H—Ala—Gly—Cys—Lys—Asn($R_1$)—Phe—Phe—Trp—Lys—

-continued

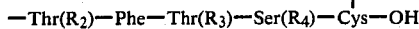
—Thr($R_2$)—Phe—Thr($R_3$)—Ser($R_4$)—Cys—OH wherein $R_1$, $R_2$, $R_3$ and $R_4$ are hydrogen or a carbohydrate moiety selected from the group consisting of hexoses and amino-hexoses modified in the 2-position with an amide group, which hexose has the pyranose structure provided that at least one R group is not hydrogen, and pharmaceutically acceptable nontoxic salts thereof.

2. A somatostatin peptide having the formula

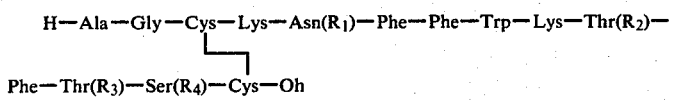
H—Ala—Gly—Cys—Lys—Asn($R_1$)—Phe—Phe—Trp—Lys—Thr($R_2$)—
Phe—Thr($R_3$)—Ser($R_4$)—Cys—Oh wherein $R_1$, $R_2$, $R_3$ and $R_4$ are hydrogen or a carbohydrate moiety selected from the group consisting of β-D-Glucopyranosyl and β-D-Glucopyranosyl modified in the 2-position with an amide group, provided that at least one R group is not hydrogen, and pharmaceutically acceptable non-toxic salts thereof.

3. The composition in accordance with claim 2 wherein $R_1$ is β-D-Glucopyranosyl.

4. The composition in accordance with claim 2 wherein $R_1$ is β-D-Glucopyranosyl modified in the 2-position with an amide group, which is linked to said Asn moiety by an amino group attached to the 1-position carbon.

5. The composition in accordance with claim 4 wherein $R_1$ is 2-acetamido-β-D-Glucopyranosyl.

* * * * *